(12) United States Patent
Vecchio et al.

(10) Patent No.: US 11,221,424 B2
(45) Date of Patent: Jan. 11, 2022

(54) METHOD FOR CALIBRATING A COLLIMATOR AND APPARATUS FOR X-RAY ANALYSIS CONFIGURED TO CARRY OUT THE METHOD

(71) Applicant: IMS GIOTTO S.P.A., Sasso Marconi (IT)

(72) Inventors: Sara Vecchio, Casalecchio di Reno (IT); Paolo Vignoli, San Giovanni in Persiceto (IT); Valerio Salomoni, Bologna (IT)

(73) Assignee: IMS GIOTTO S.P.A., Sasso Marconi (IT)

( * ) Notice: Subject to any disclaimer, the term of this patent is extended or adjusted under 35 U.S.C. 154(b) by 0 days.

(21) Appl. No.: 16/245,954

(22) Filed: Jan. 11, 2019

(65) Prior Publication Data
US 2019/0219714 A1     Jul. 18, 2019

(30) Foreign Application Priority Data
Jan. 15, 2018   (IT) ................. 102018000000868

(51) Int. Cl.
| G01D 18/00 | (2006.01) |
| G01T 7/00 | (2006.01) |
| A61B 6/00 | (2006.01) |
| A61B 6/06 | (2006.01) |
| G21K 1/02 | (2006.01) |
| A61B 6/02 | (2006.01) |

(52) U.S. Cl.
CPC ............... *G01T 7/005* (2013.01); *A61B 6/06* (2013.01); *A61B 6/584* (2013.01); *A61B 6/585* (2013.01); *G21K 1/02* (2013.01); *A61B 6/025* (2013.01); *A61B 6/4452* (2013.01); *G06T 2207/10116* (2013.01)

(58) Field of Classification Search
CPC .......... G01T 7/005; A61B 6/06; A61B 6/584; A61B 6/585; A61B 6/025; A61B 6/4452; A61B 6/40; G21K 1/02; G06T 2207/10116
USPC ........................................................ 378/207
See application file for complete search history.

(56) References Cited

U.S. PATENT DOCUMENTS

| 6,215,853 | B1 * | 4/2001 | Kump ................. A61B 6/06 378/147 |
| 6,322,249 | B1 * | 11/2001 | Wofford ............. A61N 5/1049 378/152 |
| 6,402,373 | B1 * | 6/2002 | Polkus ................ G01D 18/00 378/207 |
| 6,478,462 | B2 * | 11/2002 | Polkus ................ A61B 6/4233 378/205 |
| 6,502,985 | B1 * | 1/2003 | Garland .............. G21K 1/04 378/150 |

(Continued)

FOREIGN PATENT DOCUMENTS

DE      102012205261 A1    10/2013

OTHER PUBLICATIONS

Italian Search Report dated Sep. 26, 2018 from counterpart IT App No. 2018000000868.

*Primary Examiner* — Kiho Kim
(74) *Attorney, Agent, or Firm* — Shuttleworth & Ingersoll, PLC; Timothy Klima

(57) ABSTRACT

The present invention relates to a method for calibrating a collimator of X-rays and an apparatus for X-ray analysis which comprises the collimator and can carry out the method automatically.

10 Claims, 4 Drawing Sheets

(56) References Cited

U.S. PATENT DOCUMENTS

| | | | |
|---|---|---|---|
| 7,327,830 B2* | 2/2008 | Zhang | G01N 23/04 378/147 |
| 8,582,721 B2* | 11/2013 | Takahashi | A61B 6/06 378/116 |
| 8,827,555 B2* | 9/2014 | Thwaite | A61N 5/1075 378/207 |
| 2002/0015474 A1* | 2/2002 | Tybinkowski | G21K 1/025 378/153 |
| 2002/0080923 A1* | 6/2002 | Boomgaarden | A61B 6/588 378/207 |
| 2002/0122534 A1* | 9/2002 | Polkus | A61B 6/587 378/205 |
| 2002/0126799 A1* | 9/2002 | Saladin | G21K 1/04 378/152 |
| 2005/0152498 A1* | 7/2005 | Mungilwar | G21K 1/04 378/97 |
| 2005/0169432 A1 | 8/2005 | Groh et al. | |
| 2007/0041508 A1* | 2/2007 | Tubbs | A61B 6/583 378/207 |
| 2012/0203490 A1* | 8/2012 | Sayeh | A61N 5/1075 702/105 |
| 2013/0284951 A1* | 10/2013 | Echner | G21K 1/046 250/505.1 |
| 2013/0343518 A1* | 12/2013 | Noo | A61B 6/06 378/19 |
| 2014/0016742 A1* | 1/2014 | Sall | A61B 6/06 378/37 |
| 2014/0185746 A1* | 7/2014 | Baturin | G21K 1/06 378/36 |
| 2016/0361567 A1* | 12/2016 | Chappelow | A61N 5/1045 |
| 2016/0361568 A1* | 12/2016 | Chappelow | G06T 7/0012 |
| 2017/0225015 A1* | 8/2017 | Thieme | A61B 6/5258 |
| 2018/0250531 A1* | 9/2018 | Ansorge | G01N 23/20 |

* cited by examiner

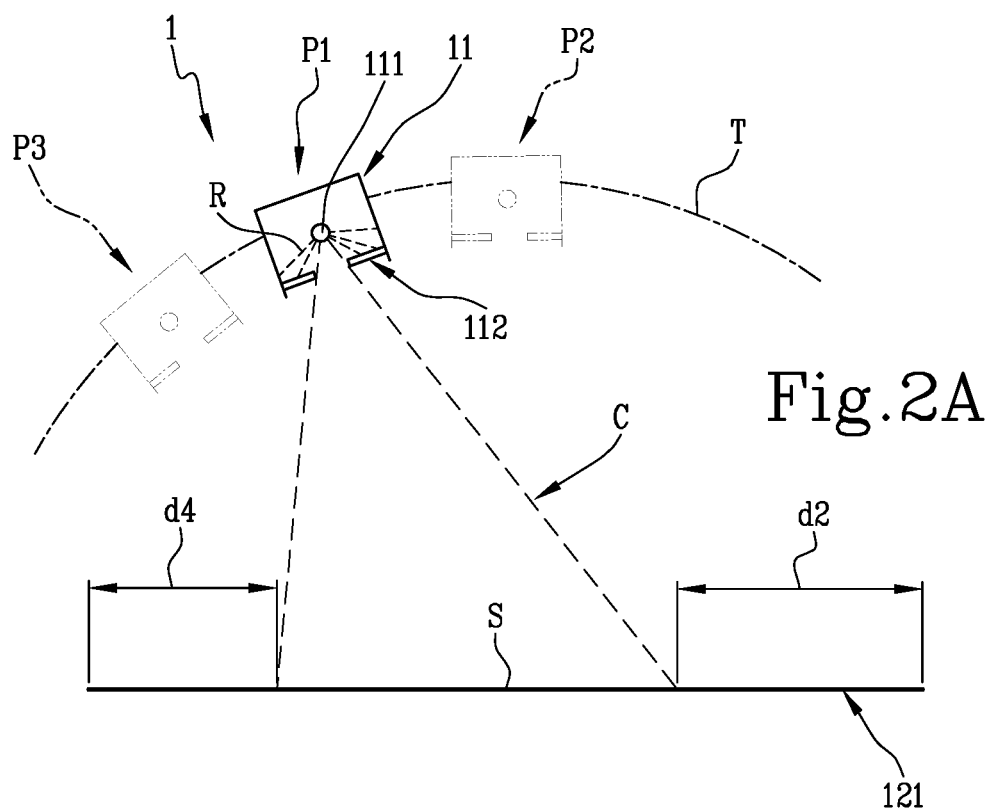
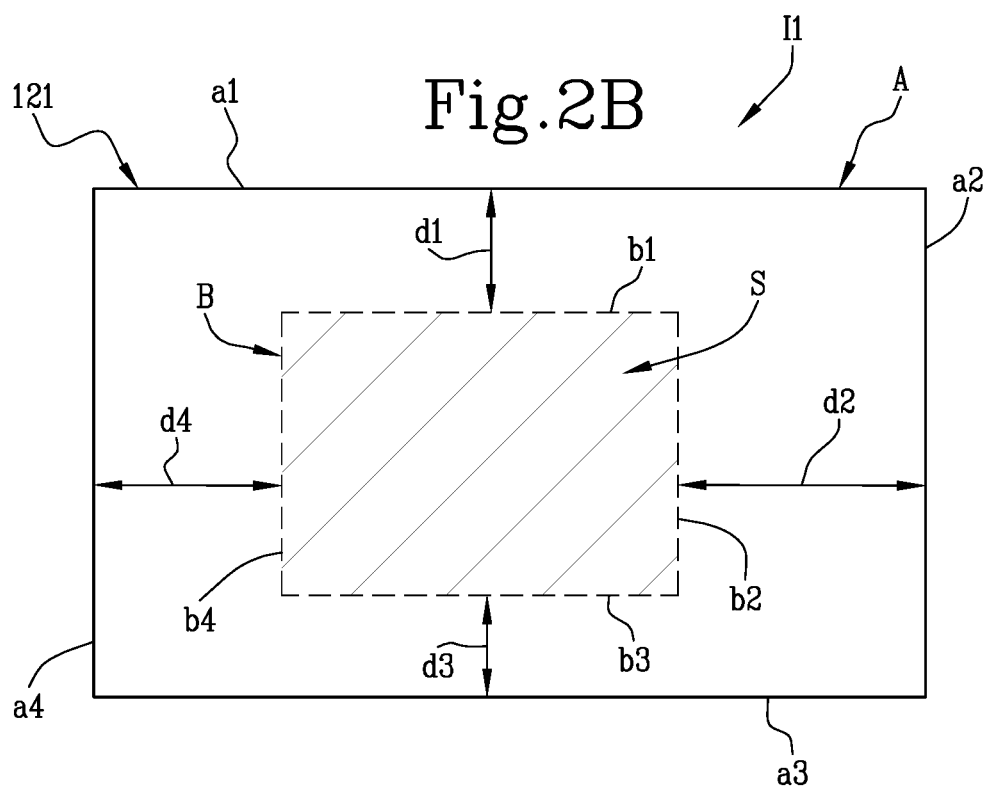

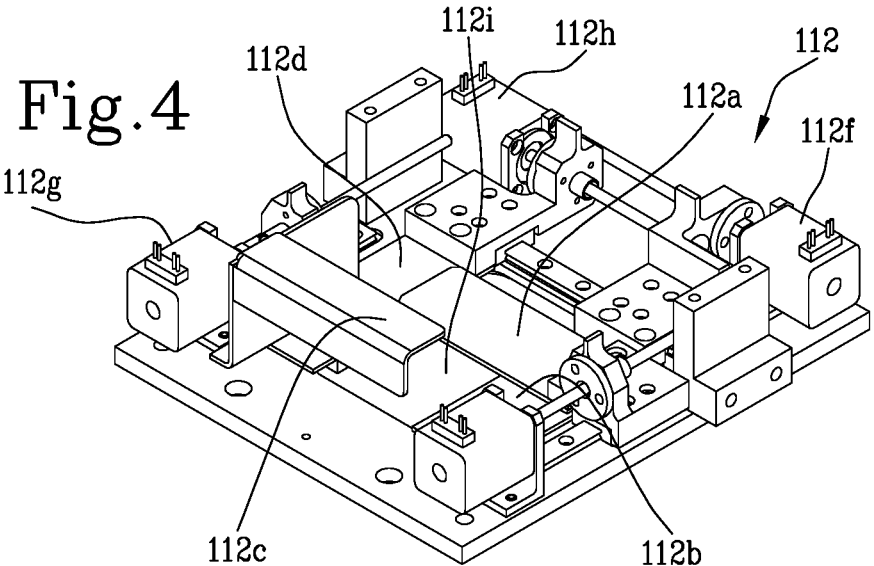
Fig.4
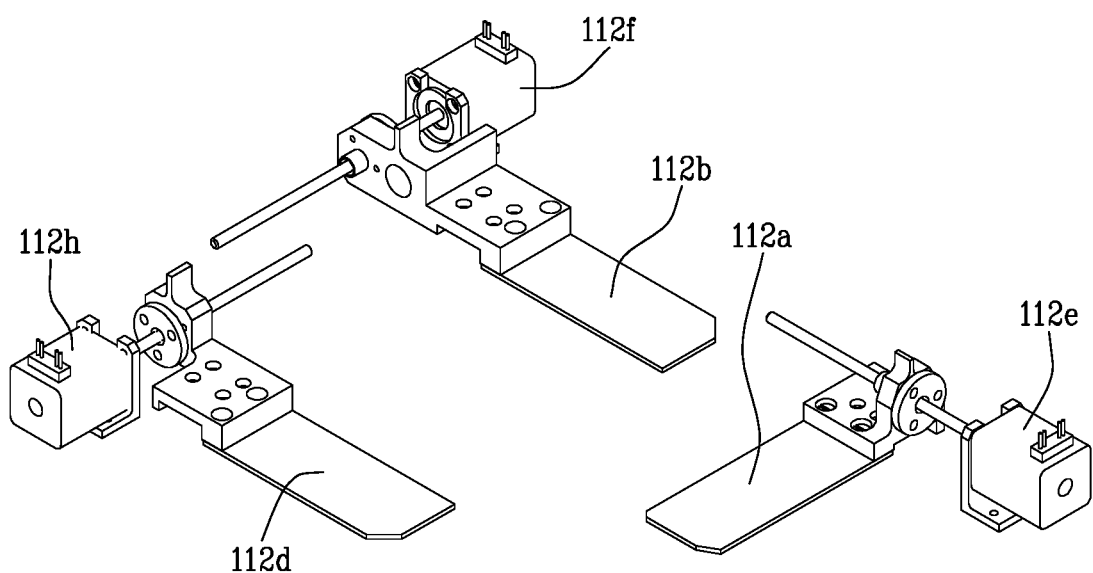
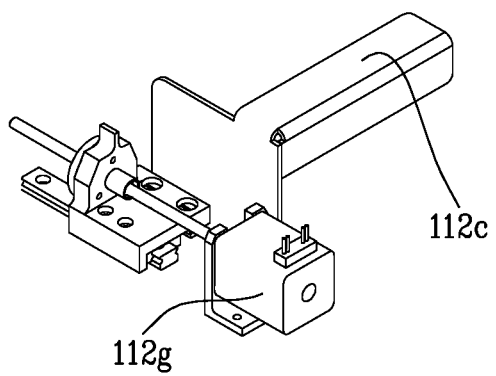
Fig.5

METHOD FOR CALIBRATING A COLLIMATOR AND APPARATUS FOR X-RAY ANALYSIS CONFIGURED TO CARRY OUT THE METHOD

This application claims priority to Italian Patent Application 102018000000868 filed Jan. 15, 2018, the entirety of which is incorporated by reference herein.

The present invention relates to a method for calibrating a collimator for the collimation of X-rays and an apparatus for X-ray analysis which comprises the collimator and can carry out the method automatically.

Apparatus for analysing X-rays for diagnostic purposes allow the user to adjust the field of X-rays generated so that the operating condition that the field adopts is the best suited to the shape and/or size and/or characteristics of the object to be analysed.

The object could be a part of a person's body.

The operating condition of the field is to be understood in the sense that a variation of the operating condition corresponds to a variation of the shape and/or at least one dimension and/or the orientation of the field.

The operating condition of the field depends on the operating configuration of a collimator of the apparatus and the position of a device which comprises the collimator itself and a source of X-rays. The collimator collimates the X-rays of the source so as to obtain the field of X-rays.

Such apparatus comprise an interface by means of which the end user, for example an X-ray technician, can select, for the purposes of the X-ray analysis, the operating condition of the field C. In the event that it is necessary to change at least one possibility of selection by the end user, in the sense that it is necessary to set a new selection function whereby the end user can select a new operating condition which was not previously selectable, the intervention of a technical service user is required.

The technical service user does not know a priori what the effect will be of varying the operating configuration of the collimator and/or varying the position of the device on the operating condition of the field.

Therefore, he has to proceed on a trial and error basis, which can take a long time. The object of the present disclosure is to provide an apparatus for X-ray analysis, a calibrating method for calibrating a collimator belonging to the apparatus, and a programming method for programming an interface of the apparatus, which enable this drawback to be overcome.

This object is fully achieved by a method having features as disclosed herein and/or by an apparatus having features as disclosed herein.

There exists an apparatus for X-ray analysis described in patent document US 2002/122534. The apparatus described in patent document US 2002/122534 is configured to take into account the effect of varying the operating configuration of the collimator on the operating condition of the field by using mathematical formulas. Such mathematical formulas, which correlate the variation of the operating configuration of the collimator with the variation of the operating condition of the field, can vary in the event of a replacement of the collimator or a change in the distance between the source and collimator. The apparatus described in US 2002/122534 thus requires the technical service user to "manually" update the mathematical formulas on the basis of a priori knowledge of the geometry of the system, in the event that any component of the apparatus involved in defining the operating condition of the field is changed, since such a change makes it necessary to reset the aforesaid mathematical formulas. In general, any change, also in the type of components external to the collimator and/or in their reciprocal position, could influence the correlation between the variation of the operating configuration of the collimator and the variation of the operating condition of the field, requiring the user to quantify the entity of such variations to ensure a correct updating of the mathematical formulas.

Another apparatus for X-ray analysis is described in the patent document DE102012205261. The apparatus enables a series of X-ray images to be recorded in succession so as to obtain a compound image, but it does not enable the user to be helped either in the selection of the operating configuration of the collimator or in the operations of calibrating the apparatus in the event of changes regarding the collimator or the other components of the apparatus.

An apparatus for X-ray analysis and/or a method for calibrating a collimator belonging to the apparatus, in accordance with the present disclosure, make it possible to overcome the drawback due to the necessity of having to "manually" recalibrate the apparatus in the above-mentioned cases in which a change occurs in the type of collimator and/or in the type and/or reciprocal position of the other components of the apparatus.

The features of an apparatus in accordance with the present disclosure, of a calibration method in accordance with the present disclosure, and of a programming method in accordance with the present disclosure will be clarified by the following detailed description relating to respective embodiments of said apparatus, calibration method and programming method, offered by way of non-limiting example of the claimed concepts.

The following detailed description refers to the appended drawings, in which:

FIGS. 2A and 2B illustrate a first operating situation in which that possible embodiment of the apparatus can be found;

FIGS. 4 and 5 are views of a possible example of a collimator which can be part of that possible embodiment of the apparatus, in an assembled condition and in an exploded view, respectively.

Figure 1A:
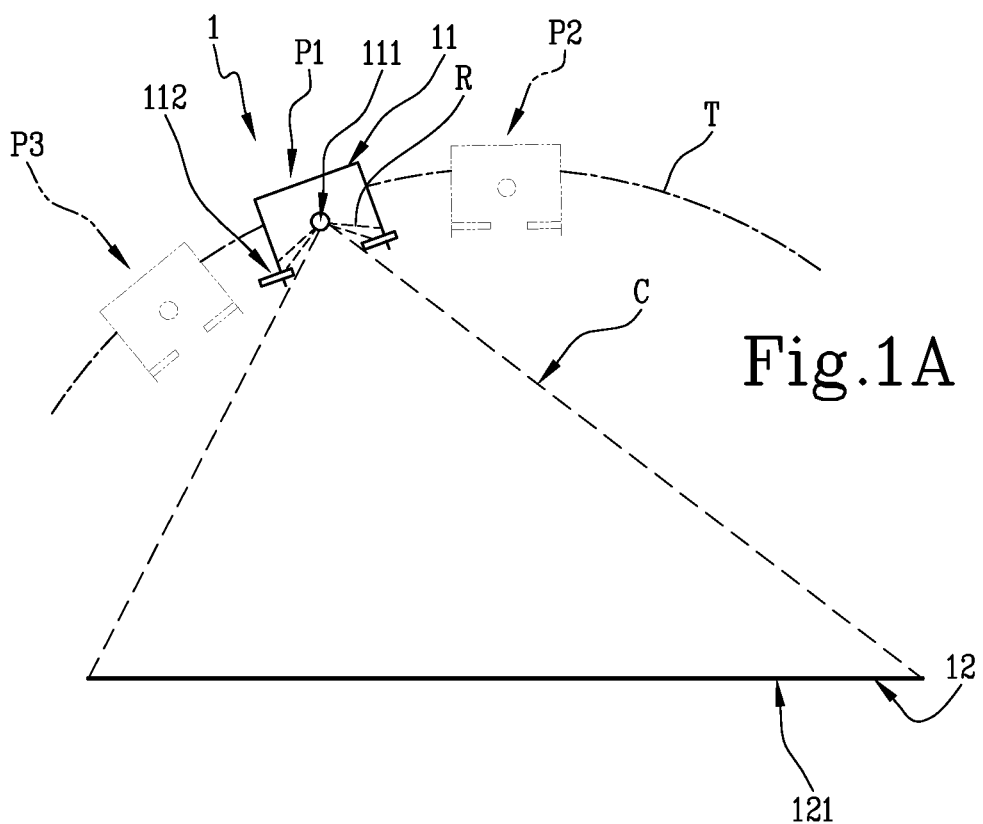
FIGS. 1A and 1B illustrate a preliminary operating situation in which a possible embodiment of an apparatus in accordance with the present disclosure can be found.
Figure 3A:
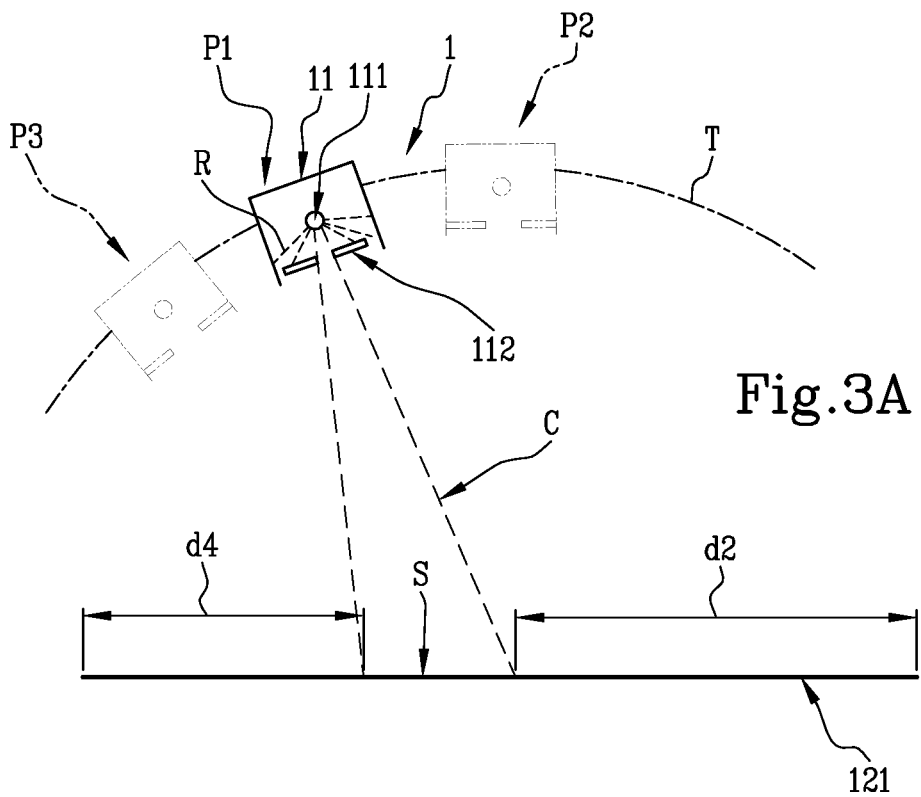
FIGS. 3A and 3B illustrate a second operating situation in which that possible embodiment of the apparatus can be found.

A possible embodiment of an apparatus in accordance with the present disclosure is denoted by 1 in FIGS. 1A, 2A and 3A.

The apparatus 1 is configured for X-ray analysis. The X-ray analysis could be performed, for example, for medical and/or diagnostic purposes.

Figure 1B:
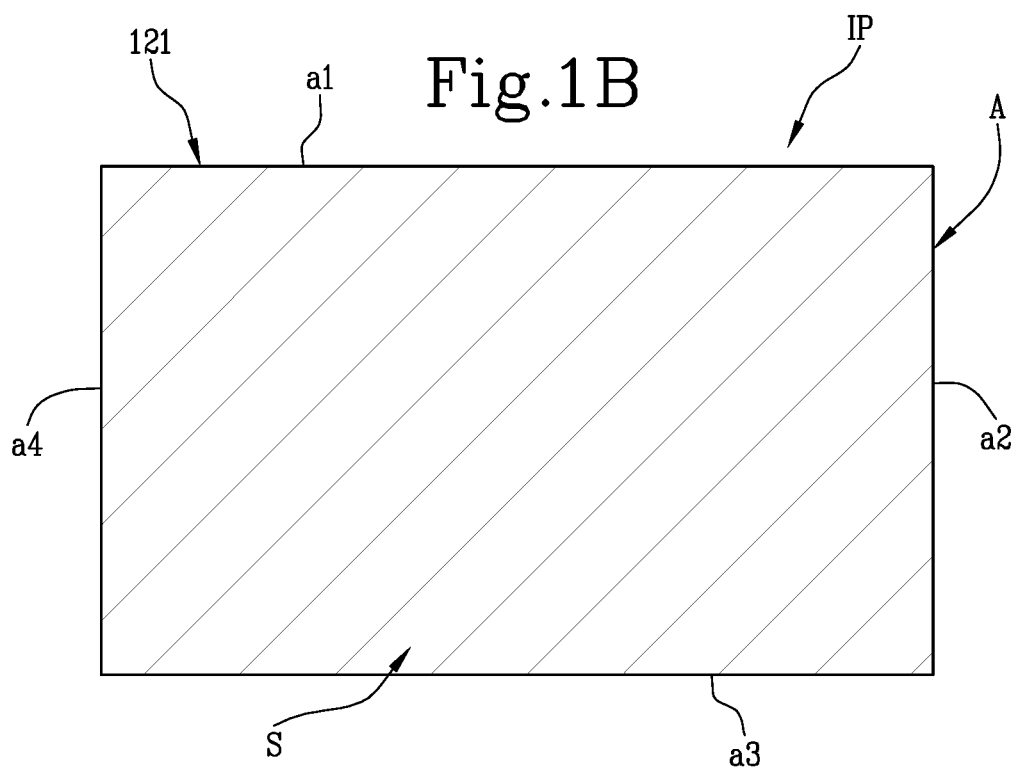
Figure 3B:
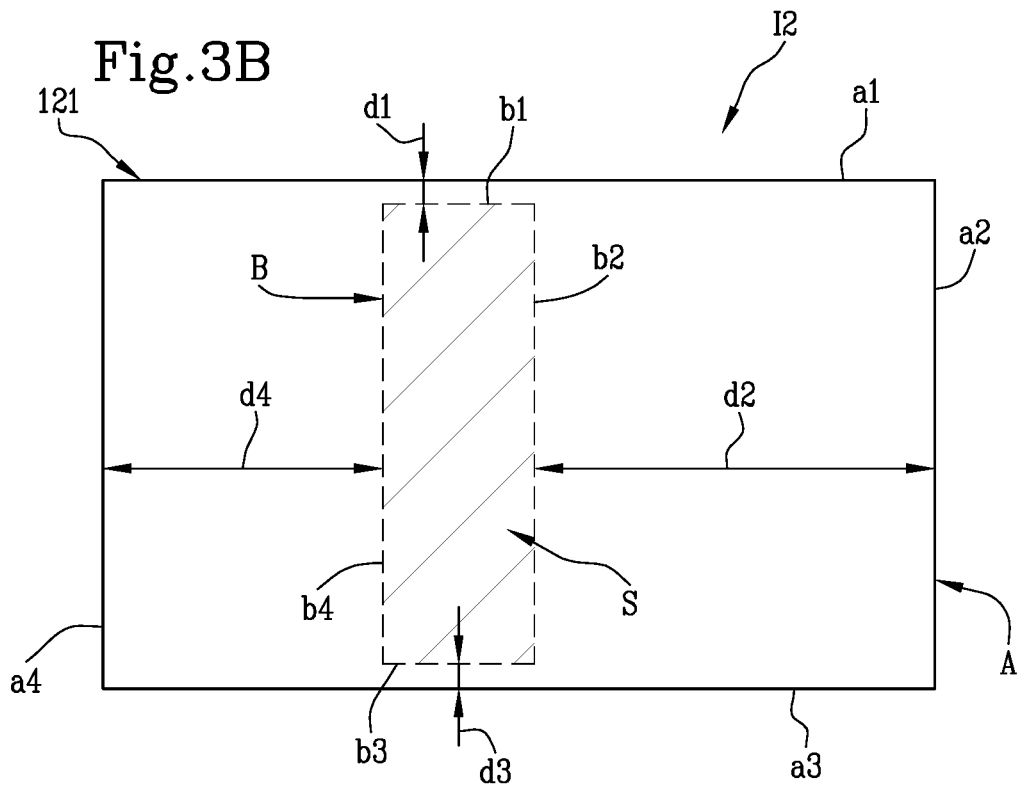

FIGS. 1A and 1B refer to a preliminary operating situation in which the apparatus 1 may be found. FIGS. 2A and 2B refer to a first operating situation in which the apparatus 1 may be found. FIGS. 3A and 3B refer to a second operating situation in which the apparatus 1 may be found.

In FIGS. 1A, 2A and 3A, only some components of the apparatus 1 are schematically shown. Therefore, the apparatus 1 can also comprise other components.

The apparatus comprises a device 11. The device 11 is configured to generate a field of X-rays.

The field of X-rays is schematically shown and denoted by C in FIGS. 1A, 2A and 3A.

The device 11 comprises a source 111 and a collimator 112. The source 111 is configured to generate X-rays. The X-rays are denoted by R. The device 11 is configured so that the collimator 112 collimates the rays generated by the source 111, in such a way as to define the field C.

The apparatus comprises a detector 12. The detector 12 is configured to detect X-rays. The X-ray detector comprises a detection surface 121. As regards the detector 12, only the detection surface 121 is shown in FIGS. 1A, 2A and 3A.

The detection surface 121 is shown schematically and in profile in FIGS. 1A, 2A and 3A.

The detector 12 is configured to reveal one or more images of the detection surface 121. The detector 12 is configured so that each of the one or more images shows the detection surface 121 and is representative of the X-rays incident on the detection surface 121.

A preliminary image revealed by the detector is shown in FIG. 1B. The preliminary image is denoted by "IP". A first image revealed by the detector is shown in FIG. 2B. The first image is denoted by "I1". A second image revealed by the detector is shown in FIG. 3B. The second image is denoted by "I2".

Each of the images shows the detection surface 121 in a plan view.

The apparatus 1 is configured to cause a variation of the position of the device 11 relative to the detection surface 121. The apparatus 1 is configured to cause the variation of the position of the device 11 by moving the device 11. The movement could take place along a trajectory. In FIGS. 1A, 2A and 3A, the trajectory is denoted by T. The trajectory could be, for example, an arc. The variation of the position of the device 11 relative to the detection surface 121 implies a corresponding variation of the position of the source 111 and a corresponding variation of the position of the collimator 112 relative to the detection surface 121, in such a way that the collimator 112 follows the variation of the position of the source 111.

Through this movement, the device 11 can adopt a plurality of different positions of the device 11 relative to the detection surface 121. In FIGS. 1A, 2A and 3A, the device 11, where represented with a continuous line, is in a first position, denoted by P1. In FIGS. 1A, 2A and 3A, the device 11, where represented with a broken line, is in a second position and in a third position relative to the detection surface 121. The second and third positions are denoted by P2 and P3, respectively. The first position P1 and second position P2 are different from each other. The second position P2 and third position P3 are different from each other.

The collimator 112 can adopt a plurality of operating configurations. The operating configurations correspond to a plurality of respective collimation modes with which the collimator 112 can collimate the X-rays generated by the source 111. When it adopts one of the operating configurations, the collimator 112 collimates the X-rays in accordance with the collimation mode that corresponds to the operating configuration adopted by the collimator 112. The variation of the operating configuration of the collimator corresponds to a variation of the collimation mode of the collimator 112.

The collimator 112 comprises a plurality of lamellas (blades). The lamellas can be in any number. A view of an example of a collimator 112 is shown in FIGS. 4 and 5. FIG. 4 shows that example of a collimator in an assembled condition. FIG. 5 shows that example of a collimator 112 in an exploded view. The lamellas (blades) in FIGS. 4 and 5 are denoted by 112a, 112b, 112c and 112d.

The collimator 112 defines a passage window for the passage of the X-rays generated by the source. The passage window is defined between the lamellas of the collimator 112. The passage window, as regards the example of a collimator shown in FIGS. 4 and 5, is denoted by 112i.

Geometrical configuration of the passage section 112i can mean the shape and/or at least one dimension of the passage window and/or more than one dimension of the passage window and/or the positioning of the passage window 112i relative to the source 111. The variation of the geometrical configuration of the passage window 112i can correspond to a variation of the positioning of the passage window 112i relative to the source 111, and/or of the shape of the passage window 112i, and/or of at least one dimension or more than one dimension of the passage window 112i. Positioning of the passage window 112i relative to the source 111 means a positioning relative to a reference system integral with the source 111.

The collimator 112 is configured to cause a variation of the geometrical configuration of the passage window 112i. The variation of the geometrical configuration of the passage window 112i corresponds to a variation of the operating configuration of the collimator 112. Each of the operating configurations of the collimator corresponds to a respective geometrical configuration of the passage window 112i.

The collimator 112 is configured to cause a variation of the position of each of the lamellas relative to the source 11. The variation of the combination of positions of the respective lamellas relative to the source 111 corresponds to the variation of the geometrical configuration of the passage window, and thus also to the variation of the operating configuration of the collimator 112. Each of the operating configurations of the collimator 112 corresponds to a respective geometrical configuration of the passage window, and therefore also to a respective combination of positions of the respective lamellas relative to the source 111.

The collimator 112, in order to cause a variation of the position of each of the lamellas relative to the source, comprises a plurality of motors. In FIGS. 4 and 5, the motors are denoted by 112e, 112f, 112g, and 112h.

Each of the motors is associated with a respective lamella in order to be able to cause the variation of the position of the respective lamella relative to the source 111. The variation of an operating parameter of any one of the motors causes a variation of the position, relative to the source 111, of the lamella with which that motor is associated. The operating parameter can be, for example, the number of revolutions made by a shaft of the motor and/or a position of the shaft of the motor.

In the example of a collimator shown in FIGS. 4 and 5, a first motor 112e is associated with a first lamella 112a, a second motor 112f is associated with a second lamella 112b, a third motor 112g is associated with a third lamella 112c, and a fourth motor 112h is associated with a fourth lamella 112d.

The collimator 112 is configured to cause a variation of the operating parameter of each of the motors. The variation of the combination of operating parameters of the respective motors corresponds to the variation of the combination of positions of the respective lamellas relative to the source 111, and therefore also to the variation of the geometrical configuration of the passage window, and therefore also to the variation of the operating configuration of the collimator. Each of the operating configurations of the collimator 112 corresponds to a respective combination of positions of the respective lamellas relative to the source 111, and therefore to a respective combination of operating parameters of the respective motors.

In the preliminary operating situation in FIGS. 1A-1B, in the first operating situation in FIGS. 2A-2B, and in the second operating situation in FIGS. 3A-3B, the collimator 112 is adopting respectively:

- a preliminary operating configuration corresponding to a preliminary geometrical configuration of the passage window 112i and therefore to a preliminary combination of positions of the respective lamellas and therefore to a preliminary combination of operating parameters of the respective motors;
- a first operating configuration corresponding to a first geometrical configuration of the passage window 112i and therefore to a first combination of positions of the respective lamellas and therefore to a first combination of operating parameters of the respective motors;
- a second operating configuration corresponding to a second geometrical configuration of the passage window 112i and therefore to a second combination of positions of the respective lamellas and therefore to a second combination of operating parameters of the respective motors.

The apparatus 1 is configured so that the field C can adopt a plurality of operating conditions. Each of the operating conditions of the field C can be considered as an operating condition of the apparatus 1.

Each of the operating conditions of the field C and/or of the apparatus 1 corresponds to a respective combination of an operating configuration of the collimator 112 and position of the device 11 relative to the detection surface 121. The variation of the combination of the position of the device 11 relative to the detection surface 121 and the operating configuration of the collimator 112 corresponds to and/or causes a variation of the operating condition of the field C. The operating condition of the field C and/or of the apparatus 1 therefore depends on the operating configuration of the collimator 112 and the position of the device 11 relative to the detection surface 121.

In general, the operating conditions that the field C and/or the apparatus 1 can adopt differ from one another at least in one dimension of the field and/or in more than one dimension of the field C and/or in the orientation of the field C relative to the detection surface 121 and/or in the positioning of the field C relative to the detection surface 121. If one considers the field C as having the shape of a cone or truncated cone, as shown for the sake of simplicity in FIGS. 1A, 2A and 3A, the operating conditions can be considered different at least in the position of the vertex of the cone, which is established by the position of the device 11 relative to the detection surface 12, and/or in the size of the angle of the cone, which is established by the operating configuration of the collimator 112.

The apparatus 1 is configured so that, under all the operating conditions of the plurality, the field C strikes the detection surface 121 in such a way as to define an intersection section between the field C and the detection surface 121. The intersection section is denoted by S in FIGS. 1B, 2B and 3B.

The variation of the field of X-rays in general causes a variation of the geometrical configuration of the intersection section S.

Geometrical configuration can mean the shape and/or at least one dimension and/or more than one dimension and/or the positioning of the intersection section S relative to the detection surface 121. The variation of the geometrical configuration of the intersection section S can correspond to a variation of the positioning of the intersection section S relative to the detection surface 121, and/or of the shape of the intersection section S, and/or of at least one dimension of the intersection section S and/or of more than one dimension of the intersection section S. Positioning of the intersection section S relative to the detection surface 121 means a positioning relative to a reference system integral with the detection surface 12.

Hereinafter, "local" variation of the operating condition of the field C and/or of the apparatus 1 will mean a variation of the operating condition of the field while the device 11 remains fixed in a given position. The given position can for example be the first position P1 shown in FIGS. 1A, 2A and 3A.

Hereinafter, "local" variation of the geometrical configuration of the intersection section S will mean the variation of the geometrical configuration of the intersection section S while the device 11 remains fixed in the aforesaid given position. The given position, as noted above, can for example be the first position P1 as shown in FIGS. 1A, 2A and 3A.

The aforesaid local variation of the operating condition of the field C corresponds to the local variation of the geometrical configuration of the intersection section S.

Considering the device 11 to be fixed in the aforesaid given position, which, as noted above, can for example be the first position P1 of FIGS. 1A, 2A, and 3A, the variation of the operating configuration of the collimator 112 causes and/or corresponds to the local variation of the operating condition of the field C and/or of the apparatus 1, and therefore causes and/or corresponds to the local variation of the geometrical configuration of the intersection section S.

Therefore, considering the device 11 to be fixed in the aforesaid given position, which, as noted above, can for example be the first position P1 of FIGS. 1A, 2A, and 3A, each operating configuration of the collimator 112 corresponds to a respective operating condition of the field C and/or of the apparatus 1, and therefore to a respective geometrical configuration of the intersection section S.

The preliminary operating condition of the field C, the first operating condition of the field C, and the second operating condition of the field C, as per the respective pairs of FIGS. 1A-1B, 2A-2B, and 3A-3B, correspond respectively to the pair of the preliminary operating condition of the field C-preliminary geometrical configuration of the intersection section S, the pair of the first operating condition of the field C-first geometrical configuration of the intersection section S, and the pair of the second operating condition of the field C-second geometrical configuration of the intersection section S.

The intersection section S has an edge B which delimits the intersection section S. The edge B of the intersection section S comprises a plurality of sectors of the edge.

The number of the sectors can be any number, since an edge which delimits the intersection section S can be divided into any number of sectors. It could in any case be considered that each of the sectors defines a respective side of the edge B of the intersection section S.

In FIGS. 1B, 2B and 3B, the edge B of the intersection section S is divided into four sectors b1, b2, b3 and b4, which are four respective sides of the same edge B.

The position of each of the sectors of the edge B of the intersection section S relative to the detection surface 121 can be considered as the position of the sector relative to the above-mentioned reference system integral with the detection surface 121. The position of the sector can be considered as the position of a reference point of the sector. The reference point could be considered as a midpoint of the sector.

Considering the device 11 to be fixed in the aforesaid given position, which, as noted above, can for example be the first position P1 of FIGS. 1A, 2A, and 3A, the variation of the geometrical configuration of the intersection section S could for example correspond to a variation of the combination of positions of the respective sectors of the edge B of the intersection section S relative to the detection surface 121.

Therefore, considering the device 11 to be fixed in the aforesaid given position, which, as noted above, can for example be the first position P1 of FIGS. 1A, 2A, and 3A, each geometrical configuration of the intersection section S corresponds to a respective combination of positions of the respective sectors of the edge B of the intersection section S relative to the detection surface 121.

In the preliminary operating situation of FIGS. 1A-1B, in the first operating condition of FIGS. 2A-2B and in the second operating condition of FIGS. 3A-3B, the field C and/or the apparatus 1 adopts, respectively:
- a preliminary operating condition, which corresponds to the combination of the first position P1 of the device 11 with the preliminary operating configuration of the collimator 112, and therefore with a preliminary combination of positions, relative to the detection surface 121, of the respective sectors of the edge B of the intersection section S; a first operating condition, which corresponds to the combination of the first position P1 of the device 11 with the first operating configuration of the collimator 112, and therefore with a first combination of positions, relative to the detection surface 121, of the respective sectors of the edge B of the intersection section S;
- a second operating condition, which corresponds to the combination of the first position P1 of the device 11 with the second operating configuration of the collimator 112, and therefore with a second combination of positions, relative to the detection surface 121, of the respective sectors of the edge B of the intersection section S.

The apparatus 1 is configured so that each sector of the edge B of the intersection section S is associated with a respective lamella of the collimator 112. The variation of the position of any lamella relative to the source 111 causes and/or corresponds to a variation of the position, relative to the detection surface 121, of the sector associated with the lamella.

In the example of the apparatus 1 as shown in the appended figures, the variations of the operating parameters of the first motor 112e, the second motor 112f, the third motor 112g, and the fourth motor 112h cause the variation of the position, relative to the source 112, of the first lamella 112a, the second lamella 112b, the third lamella 112c and the fourth lamella 112d, respectively, and therefore the variation of the position, relative to the detection surface 121 of the first sector b1, the second sector b2, the third sector b3, and the fourth sector b4, respectively, of the edge B of the intersection section S.

The detection surface has an edge A which delimits the detection surface 121. The edge A of the detection surface 121 comprises a plurality of sectors of the edge A of the detection surface 12. The number of the sectors of the edge A of the detection surface 12 can be any number, since an edge which delimits the detection surface 12 can be divided into any number of sectors. It could in any case be that each of the sectors defines a respective side of the edge A of the detection surface 12.

In FIGS. 1B, 2B and 3B the edge A of the detection surface 121 is divided into four sectors a1, a2, a3 and a4, which are four respective sides of the same edge A.

Each of the above-mentioned sectors of the edge B of the intersection section S can be considered associated with a respective sector of the edge A of the detection surface 121, since it is turned towards that respective sector of the edge A of the detection surface A.

The position of each of the sectors of the edge B of the intersection section S can be considered as the distance between the reference point of the respective sector of the edge B and the respective associated sector of the edge A of the detection surface 121.

The position of each of the sectors of the edge B of the intersection section S can be considered as the distance between the reference point of the respective sector of the edge B and a reference point of the respective associated sector of the edge A. The reference point of the sector of the edge A could be considered as a midpoint of the sector of the sector.

In FIGS. 1B, 2B and 3B, the first sector b1, the second sector b2, the third sector b3 and the fourth sector b4 of the edge B of the intersection section S are associated with the first sector a1, the second sector a2, the third sector a3 and the fourth sector a4, respectively, of the edge A of the detection surface 121. The distances between the respective sectors b1-b4 of the edge B of the intersection section S and the respective sectors a1-a4 of the edge A of the detection surface 121 are denoted by d1, d2, d3 and d4, respectively.

Hereinafter, mathematical relationship will mean a mathematical entity which puts two or more variables mathematically in relation or correlation with each other.

A "local mathematical relationship" can be considered. This local mathematical relationship, considering the device 11 to be fixed in the aforesaid given position, mathematically correlates with each other the variation of the operating configuration of the collimator 112 and the local variation of the geometrical configuration of the intersection section S relative to the detection surface 121.

The local mathematical relationship, considering the device 11 to be fixed in the aforesaid given position, enables the geometrical configuration of the intersection section S relative to the detection surface 12 to be known if the operating configuration of the collimator 112 is known. The local mathematical relationship, considering the device 11 to be fixed in the aforesaid given position, enables the variation of the geometrical configuration of the intersection section S relative to the detection surface 121 to be known if the variation of the operating configuration of the collimator 112 is known.

For any of the lamellas it is possible to consider a local mathematical function associated with the lamella. The local mathematical function associated with the lamella mathematically correlates with each other the position relative to the detection surface 121 of the sector of the edge B associated with the same lamella and the operating parameter of the motor associated with the same lamella. The local mathematical function associated with the lamella, considering the device 11 to be fixed in the aforesaid given position, enables the position relative to the detection surface 121 of the sector associated with the same lamella to be known if the operating parameter of the motor associated with the same lamella is known. The local mathematical function, considering the device 11 to be fixed in the aforesaid given position, enables the variation of the position relative to the detection surface 121 of the sector associated with the same lamella to be known if the variation of the operating parameter of the motor associated with the same lamella is known. As noted above, the operating parameter could be a number of revolutions of the motor.

The mathematical function associated with the lamella could be a first order one, in which case the local mathematical function is to be considered a straight line that puts into relation the operating parameter of the motor associated with the same lamella and the position of the sector associated with the same lamella.

It is possible to consider a local mathematical function associated with the first lamella, which correlates the position relative to the detection surface 121 of the first sector b1 with the operating parameter of the first motor 112e, a local mathematical function associated with the second lamella, which correlates the position relative to the detection surface 121 of the second sector b2 with the operating parameter of the second motor 112f, a local mathematical function associated with the third lamella, which correlates the position relative to the detection surface 121 of the third sector b3 with the operating parameter of the third motor 112g, and a local mathematical function associated with the fourth lamella, which correlates the position relative to the detection surface 121 of the fourth sector b4 with the operating parameter of the fourth motor 112h.

The local mathematical relationship could comprise at least one local mathematical function associated with one of the lamellas.

The local mathematical relationship could comprise, for each of the lamellas, the respective local mathematical function associated with the respective lamella.

The local mathematical relationship could therefore comprise one or more of the aforesaid local mathematical functions associated, respectively, with the first lamella 112a, the second lamella 112b, the third lamella 112c and the fourth lamella 112d.

A calibration method in accordance with the present disclosure comprises a step of preparing the device 11 and detector 12.

A calibration method in accordance with the present disclosure comprises an operating sequence. By carrying out the operating sequence, a calibration of the collimator 112 is carried out and/or performed. The calibration is to be considered a calibration of the collimator 112 for the aforesaid given position of the device 11. Therefore, the aforesaid "given position" can be defined as a "calibration position". The term "calibration" is to be understood as a calibration of the collimator 112, even if the expression "calibration position" refers to the device 11. The calibration position can for example be the position denoted by P1. The calibration position in this case can be considered to coincide with the first position P1.

The operating sequence comprises a positioning step. During the positioning step, the device 11 is positioned in the calibration position P1. The positioning step preferably takes place automatically.

The operating sequence comprises a preliminary setting-up step. The operating sequence comprises a first setting-up step. The operating sequence comprises a second setting-up step. During the preliminary setting-up step, first setting-up step and second setting-up step, the collimator 112 is set in the above-mentioned preliminary operating configuration, the above-mentioned first operating configuration, and the above-mentioned second operating configuration, respectively, of the collimator 112. The preliminary setting-up step, first setting-up step and second setting-up step take place automatically.

The operating sequence comprises a generating step during which the source generates the X-rays. The generating step takes place automatically.

The operating sequence comprises a preliminary collimation step. The operating sequence comprises a first collimation step. The operating sequence comprises a second collimation step. During the preliminary collimation step, first collimation step and second collimation step, the collimator 112, whilst it adopts the preliminary operating configuration, the first operating configuration and the second operating configuration, respectively, does so in such a way that the field adopts the preliminary operating condition, the first operating condition and the second operating condition, respectively. The preliminary operating condition and first operating condition are different from each other. The first operating condition and second operating condition are different from each other. The preliminary operating configuration and first operating configuration are different from each other. The first operating configuration and second operating configuration are different from each other.

The operating sequence comprises a preliminary incidence step. The operating sequence comprises a first incidence step. The operating sequence comprises a second incidence step. During the preliminary incidence step, first incidence step and second incidence step, the field C, whilst it adopts the preliminary operating condition, the first operating condition and the second operating condition, respectively, strikes the detection surface 121 in such a way that the intersection section S is characterised, respectively, by the preliminary geometrical configuration, the first geometrical configuration, and the second geometrical configuration relative to the detection surface 121. The preliminary geometrical configuration and first geometrical configuration are different from each other. The first geometrical configuration and second geometrical configuration are different from each other.

The collimation steps and/or incidence steps could be carried out and/or take place during the generating step.

The operating sequence can comprise a preliminary acquisition step. The operating sequence comprises a first acquisition step. The operating sequence comprises a second acquisition step. During the preliminary acquisition step, first acquisition step and second acquisition step, a preliminary image IP, a first image I1 and a second image I2, respectively, are automatically acquired. The preliminary image IP, first image I1 and second image I2 are revealed by the detector 12 during the preliminary incidence step, the first incidence step and the second incidence step, respectively.

The operating sequence comprises a preliminary detection step. The operating sequence comprises a first detection step. The operating sequence comprises a second detection step. During the preliminary detection step, first detection step and second detection step, the preliminary geometrical configuration, the first geometrical configuration and the second geometrical configuration, respectively, are automatically detected. The preliminary detection step, first detection step and second detection step are carried out by automatic analysis of the preliminary image IP, the first image I1 and the second image I2, respectively.

The acquisition and detection steps can also take place during the generating step.

The operating sequence comprises a calculation step. During the calculation step the above-mentioned local mathematical relationship is automatically calculated. The calculation step is carried out automatically on the basis of and/or according to at least the first detection step and second detection step. Therefore, the local mathematical relationship is automatically calculated according to and/or on the basis of at least the first geometrical configuration of the intersection section S, second geometrical configuration of the intersection section S, first operating configuration of the collimator 112 and second operating configuration of the collimator 112. The local mathematical relationship could be automatically calculated, during the calculation step, by means of an interpolation operation carried out starting from at least:

a pair comprising the first geometrical configuration and the first operating configuration;

a pair comprising the second geometrical configuration and the second operating configuration.

The preliminary geometrical configuration is used as a reference to which the aforesaid first geometrical configuration and second geometrical configuration refer. The preliminary operating configuration of the collimator is used as a reference to which the aforesaid first operating configuration and second operating configuration refer. The local mathematical relationship comprises, for at least one of the lamellas, or for each of the lamellas, the respective local mathematical function associated with the respective lamella.

In accordance with a possible example, for each lamella, a first position of the edge associated with the respective lamella relative to the detection surface 121 and a second position of the same edge relative to the detection surface 121 could be considered. For at least one lamella, the respective first position and the respective second position of the edge associated with the respective lamella could be different from each other.

In the example, for each lamella, it could be considered that the first position of the edge associated with the respective lamella corresponds to a respective first value of the operating parameter of the motor associated with the respective lamella, and that the second position of the same edge corresponds to a respective second value of the operating parameter of the motor associated with the respective lamella In the example, it could be considered that the first geometrical configuration corresponds to a combination of positions of the respective edges relative to the detection surface, so that each edge adopts the respective first position. In the example, it could be considered that the second geometrical configuration corresponds to a combination of positions of the respective edges relative to the detection surface, so that each edge adopts the respective second position.

For at least one of the lamellas, or for each of the lamellas, the local mathematical function associated with the lamella could be automatically calculated, during the calculation step, by means of an interpolation operation carried out starting from at least:

a pair comprising the first position of the edge associated with the respective lamella and the first value of the operating parameter of the motor associated with the respective lamella;

a pair comprising the second position of the edge associated with the respective lamella and the second value of the operating parameter of the motor associated with the respective lamella. A calibration method in accordance with the present disclosure is aimed at the calibration of a collimator for collimating of X-rays.

A calibration method in accordance with the present disclosure can be carried out by means of an apparatus in accordance with the present disclosure.

An apparatus in accordance with the present disclosure is configured to carry out a calibration method in accordance with the present disclosure.

An apparatus in accordance with the present disclosure comprises an interface.

Consider a situation in which an end user wants a selection function to be implemented in the interface of the apparatus. The selection function is to be considered as a technical function by means of which the end user can ensure that the field C of X-rays is generated whilst the device 11 is in a desired position relative to the detection surface 121 and that the intersection section S is characterised by a desired geometrical configuration relative to the detection surface 121. The "desired position" and "desired geometrical configuration" are therefore to be understood as "desired" by the end user.

The desired position of the device 11 can be considered for the time being as coinciding with the above-mentioned calibration position P1.

The desired geometrical configuration is to be considered different from each of the geometrical configurations detected during the calibration method.

A programming method in accordance with the present disclosure can be used for programming the interface of an apparatus in accordance with the present disclosure.

An apparatus in accordance with the present disclosure is configured to carry out a programming method in accordance with the present disclosure.

The programming method in accordance with the present disclosure comprises a calibration method in accordance with the present disclosure.

The programming method comprises a step of implementing the above-mentioned selection function in the interface. By means of the implementation step, the selection function is implemented in the interface.

The implementation step comprises a step for receiving at least one item of geometrical data representing the desired geometrical configuration or a group of geometrical data representing the desired geometrical configuration. The at least one item of geometrical data can be entered, for example, by a technical service user who wants to implement the function.

The item of geometrical data representing the desired geometrical configuration is not to be understood as one or more physical and/or geometrical features of the apparatus, but as representative of the aforesaid desired geometrical configuration.

Considering that the desired geometrical configuration can be considered as corresponding to a desired combination of positions of the respective sectors of the edge of the intersection section S relative to the detection surface 121, the at least one item of geometrical data could comprise the desired combination.

The implementation step comprises an obtaining step. During the obtaining step, the desired operating configuration of the collimator 112 is automatically obtained as a function of the at least one item of geometrical data and by means of the local mathematical relationship calculated during the calibration method. The desired operating configuration corresponds to the desired geometrical configuration.

Thanks to the fact that the programming method comprises the calibration method in accordance with the present disclosure, even if the desired geometrical configuration is different from each of the geometrical configurations detected during the calibration method, the technical service user can quickly implement the selection function, since he only has to enter the above-mentioned at least one item of geometrical data representing the desired geometrical configuration, and need not act on a trial and error basis. In fact, the calibration method automatically obtains or calculates, by means of the local mathematical relationship, the operating configuration of the collimator 112 corresponding to the desired geometrical configuration of the intersection section S. This can be achieved since the local mathematical relationship, which is automatically calculated, and considering the device 11 to be fixed in the aforesaid given position, enables the variation of the operating configuration of the collimator 112 to be known automatically as a function of the variation of the geometrical configuration of the intersection section S relative to the detection surface 121. Therefore, thanks to the automatic calculation of the local mathematical relationship, the calibration method automatically obtains or calculates, by means of the same local mathematical relationship calculated previously, the operating configuration of the collimator 112 corresponding to the aforesaid desired geometrical configuration of the intersection section S. The apparatus is configured to carry out the calculation of the local mathematical relationship automatically and therefore to obtain or automatically calculate, by means of the same local mathematical relationship thus calculated, the operating configuration of the collimator 112 corresponding to the aforesaid desired geometrical configuration of the intersection section S.

Furthermore, a variation of the local mathematical relationship can be considered as a variation of the local mathematical relationship resulting from the above-mentioned variation of the position of the device 11 relative to the detection surface 121.

Therefore, it is possible to consider an intermediate mathematical relationship, which mathematically correlates with each other the aforesaid local mathematical relationship and the position of the device 11 relative to the detection surface 12.

The intermediate mathematical relationship enables the local mathematical relationship to be known if the position of the device 11 relative to the detection surface 121 is known. The intermediate mathematical relationship enables the variation of the local mathematical relationship to be known if the variation of the position of the device 11 relative to the detection surface 121 is known.

For any of the lamellas it is possible to consider an intermediate mathematical function associated with the lamella. The intermediate mathematical function associated with the lamella mathematically correlates with each other the position of the device 11 relative to the detection surface 121 and the local mathematical function associated with the same lamella. The intermediate mathematical function associated with the lamella enables the local mathematical function associated with the same lamella to be known if the position of the device 11 relative to the detection surface 121 is known. The intermediate mathematical function associated with the lamella enables the variation of the local mathematical function associated with the same lamella to be known if the variation of the position of the device 11 relative to the detection surface 121 is known.

The intermediate mathematical function associated with the lamella could be for example a curve. The intermediate mathematical function associated with the lamella could for example be a curve at least of the second order. The curve puts the position of the device 11 relative to the detection surface 121 into relation with the local mathematical function associated with the same lamella. The intermediate mathematical function associated with the lamella could for example be a parabola.

In general, if the local mathematical function associated with the lamella is defined by one or more coefficients, the intermediate mathematical function associated with the same lamella correlates with each other the variation of the position of the device 11 relative to the detection surface 121 and the variation of the one or more coefficients. If the local mathematical function associated with the lamella were for example a straight line defined by two coefficients, for example the angular coefficient of the straight line and the y value at zero x value of the straight line, the intermediate mathematical function associated with the same lamella could define the variation of each of the parameters of the straight line relative to the variation of the position of the device 11, and therefore the variation of the angular coefficient and of the zero x value relative to the variation of the position of the device 11.

The intermediate mathematical relationship could comprise at least one intermediate mathematical function associated with one of the lamellas.

The intermediate mathematical relationship could comprise, for each of the lamellas, the respective intermediate mathematical function associated with the respective lamella.

It is possible to consider an intermediate mathematical function associated with the first lamella, which correlates with each other the position of the device relative to the detection surface 121 and the local mathematical function associated with the first lamella, an intermediate mathematical function associated with the second lamella, which correlates with each other the position of the device relative to the detection surface 121 and the local mathematical function associated with the second lamella, an intermediate mathematical function associated with the third lamella, which correlates with each other the position of the device relative to the detection surface 121 and the local mathematical function associated with the third lamella, and an intermediate mathematical function associated with the fourth lamella, which correlates with each other the position of the device relative to the detection surface 121 and the local mathematical function associated with the fourth lamella.

The intermediate mathematical relationship could therefore comprise one or more of the aforesaid intermediate mathematical functions associated, respectively, with the first lamella 112a, the second lamella 112b, the third lamella 112c and the fourth lamella 112d.

It is possible to consider a group of positions that the device 11 can adopt relative to the detection surface 121. The positions of the group are to be considered as a part of the above-mentioned plurality of positions that the device 11 can adopt. The group of positions could for example comprise the first position P1, the second position P2, and the third position P3. The positions of the group can be considered, for reasons that will later be clear, as "calibration positions" of the device 11, although the term calibration must refer, more appropriately, as noted above, to the collimator 112.

A calibration method in accordance with the present disclosure could comprise carrying out the operating sequence for each position of the group of calibration positions of the device 11. This means that the calibration method comprises carrying out the above-mentioned operating sequence more than once. Every time that the operating sequence is carried out, the above-mentioned "calibration position" is to be considered as a respective position of the group of calibration positions.

A calibration method in accordance with the present disclosure, in such a case, comprises carrying out a further calculation step. During the further calculation step, the above-mentioned intermediate mathematical relationship is calculated automatically. Said further calculation step is carried out on the basis of the operating sequences carried out. The intermediate mathematical relationship can comprise, for at least one of the lamellas, the respective intermediate mathematical function associated with the respective lamella.

The further calculation step is carried out automatically on the basis of and/or according to at least the operating sequences carried out.

In accordance with a possible example of calculation of the intermediate mathematical relationship, the first position P1 could be considered as the first calibration position and the second position P2 as the second calibration position. In the example, it would therefore be possible to consider a first operating sequence, carried out for the first calibration position P1, and a second operating sequence, carried out for the second calibration position P2. It would therefore be possible to consider a first local mathematical relationship, calculated during the first operating sequence, and a second local mathematical relationship, calculated during the second operating sequence. In the example, the intermediate mathematical relationship could be automatically calculated, during the further calculation step, according to and/or on the basis of at least of the first local mathematical relationship, second local mathematical relationship, first position P1 and second position P2.

In the example, the further calculation step could therefore be carried out automatically on the basis of and/or according to at least the first calibration position P1, second calibration position P2, first local mathematical relationship, and second local mathematical relationship.

In the example, the intermediate mathematical relationship could be automatically calculated, during the further calculation step, by means of a interpolation operation carried out starting from at least:
- a pair comprising the first calibration position P1 and the first local mathematical relationship;
- a pair comprising the second calibration position P2 and the second local mathematical relationship.

It should be noted that the first local mathematical relationship and second local mathematical relationship can each comprise in turn, for each of the lamellas, a respective local mathematical function associated with the lamella, in accordance with what was described above. Therefore, the aforesaid first local mathematical relationship could comprise, for each of the lamellas, a respective first local mathematical function associated with the respective lamella. Accordingly, the aforesaid second local mathematical relationship could comprise, for each of the lamellas, a respective second local mathematical function associated with the respective lamella. For each lamella, the respective first local mathematical function is different from the respective second local mathematical function precisely because of the difference between the first calibration position P1 and the second calibration position P2.

For at least one of the lamellas, or for each of the lamellas, the intermediate mathematical function associated with the lamella could be automatically calculated, during the further calculation step, by means of a interpolation operation carried out starting from at least:
- a pair comprising the first calibration position P1 and the first local mathematical function associated with the respective lamella;
- a pair comprising the second calibration position P2 and the second local mathematical function associated with the respective lamella.

The group of positions could for example comprise at least three positions.

The intermediate mathematical relationship could for example be a degenerate conic.

The intermediate mathematical relationship could for example be a parabola, in particular if the group of calibration positions comprises at least three positions.

Suppose that the local mathematical relationship calculated for each of the positions of the group comprises a straight line. In this case, therefore, the intermediate mathematical function is a parabola which mathematically correlates with each other the variation of the position of the device 11 and the variation of the straight line.

The intermediate mathematical relationship can comprise, for each of the lamellas, the respective intermediate mathematical function associated with the respective lamella.

Consider the case in which the above-mentioned desired position of the device 11 relative to the detection surface 121, selectable by means of the above-mentioned selection function, does not coincide with any of the positions of the group of calibration positions. By calculating the above-mentioned intermediate mathematical relationship, the above-mentioned advantages in terms of the rapidity with which the technical service user can implement the selection function will be obtained even if the desired position is different from each of the positions of the group of calibration positions.

In this case, during the receiving step, at least one item of position data representing the desired position of the device 11 relative to the detection surface 121 is also received. The at least one item of position data can be entered, for example, by a technical service user who wants to implement the function.

In this case the programming method comprises a first obtaining step and a second obtaining step.

During the first obtaining step, the local mathematical relationship corresponding to the desired position of the device 11 is automatically obtained as a function of the at least one item of position data and by means of the intermediate mathematical relationship calculated during the calibration method.

During the second obtaining step, the desired operating configuration of the collimator 112 corresponding to the desired geometrical configuration is automatically obtained as a function of the at least one item of geometrical data and by means of the local mathematical relationship corresponding to the desired position.

The calibration method automatically obtains or calculates, by means of the intermediate mathematical relationship, the local mathematical relationship corresponding to the desired position of the device 11. The latter local mathematical relationship enables the operating configuration of the collimator 112 corresponding to the desired geometrical configuration of the intersection section S to be automatically obtained or calculated for the desired position of the device 11.

It should be noted that a programming method in accordance with the present disclosure could be carried out in such a way that the implementation step may also be remote in time from when the at least one calibration operating sequence is carried out, since the end user's needs could change over time.

An apparatus in accordance with the present disclosure can comprise at least one computer processing system which comprises at least one processing unit. The processing system, by means of at least one software program implemented in the at least one processing unit, is configured to cause and/or carry out the calibration method in accordance with the present disclosure and/or the programming method in accordance with the present disclosure, and therefore to carry out at least each of the above-mentioned calculation steps.

An apparatus 1 in accordance with the present disclosure can comprise at least one further interface. By means of the further interface, the technical service user can cause the apparatus 1 to carry out the calibration method in accordance with the present disclosure and/or the programming method in accordance with the present disclosure. The further interface could also coincide with the above-mentioned interface in which the above-mentioned selection function is implemented.

Furthermore, it should be noted that, for each position of the device 11, and also considering the operating configuration of the collimator 112 to be fixed, the apparatus 1 could be configured to cause a shifting of the source 111 relative to the collimator 112. In this case, the shifting would therefore also contribute to causing a variation of the operating condition of the field C.

By means of an apparatus and/or a method in accordance with the present disclosure, a user can carry out a fast, automatic calibration procedure on the collimator itself every time there is a component replacement which could also give rise to a change in the mathematical link existing between the variation of the operating configuration of the collimator, the variation of the geometrical configuration of the intersection section S, and the variation of the position of the device including the collimator and source. In such a case, the user is not required to perform any manual entry of the numerical coefficients of the mathematical link, which is automatically recalculated by means of the calibration procedure without any a priori knowledge of the entity of the geometric variation.

Furthermore, the device 11 could comprise a number of sources 111, each positioned at a different distance from the collimator 112. In this case the apparatus 1 would be configured to enable the user to select which source to use, which would influence the operating condition of the field C, also with the position of the device 11 and the operating configuration of the collimator 112 being equal.

The invention claimed is:

1. A method for programming an interface of an apparatus for X-ray analysis comprising a collimator, the programming method comprising:
a method for calibrating the collimator for the collimation of X-rays, comprising:
providing a device generating a field of X-rays, the device comprising a source and a collimator and being configured so that the collimator collimates the rays of the source in such a way as to define a field of X-rays;
providing a detector comprising a detection surface and configured to reveal at least one image of the detection surface, the at least one image being representative of the X-rays incident on the detection surface;
providing that the collimator comprises a plurality of blades, the collimator being configured so as to cause a variation of the position of each of the blades relative to the source, in such a way that the variation of the operating configuration of the collimator corresponds to a variation of a combination of positions of the respective blades relative to the source;
providing that the intersection section has an edge which delimits the intersection section and which comprises a plurality of sectors of the edge;
providing that each sector of the sectors is associated with a respective one of the blades, in such a way that the variation of the position relative to the source of any of the blades causes a variation of the position relative to the detection surface of the sector associated with the any of the blades, the variation of the geometrical configuration of the intersection section corresponding to a variation of the combination of positions of the respective sectors relative to the detection surface;
providing that the collimator comprises a plurality of motors to cause the variation of the position of each of the blades relative to the source;
providing that each of the motors is associated with a respective one of the blades, so that a variation of an operating parameter of any of the motors causes the variation of the position relative to the source of the blade to which the any motor is associated, the collimator being in this way configured so that a variation of the combination of operating parameters of the respective motors causes the variation of the combination of the respective positions of the blades relative to the source;
providing a local mathematical relationship, for each of the blades, comprising a local mathematical function associated with the detection surface, the local mathematical function correlating mathematically to each other, for that calibration position of the device, the position relative to an edge of the detection surface of the sector associated with the blade and the operating parameter of the motor associated with the blade;
for at least one calibration position of the device relative to the detection surface, a calibration operating sequence, the operating sequence being for calibrating the collimator and comprising:
a positioning step during which the device is automatically positioned in the calibration position;
a generating step during which the source automatically generates the X-rays;
a first setting-up step during which the collimator is automatically set in a first operating configuration of the plurality of operating configurations;
a first collimation step during which the collimator, while in the first operating configuration, is such that the field adopts a first operating condition, the first operating condition corresponding to the combination of the calibration position of the device and the first operating configuration of the collimator;
a first incidence step during which the field, while in the first operating condition, strikes the detection surface, in such a way that the intersection section has a first geometrical configuration relative to the detection surface;
a first acquisition step during which a first image is automatically acquired, the first image being revealed by the detector during the first incidence step;

a first detection step during which the first geometrical configuration is detected automatically by analysis of the first image;

a second setting-up step during which the collimator is automatically set in a second operating configuration of the plurality of operating configurations;

a second collimation step during which the collimator, while in the second operating configuration, is such that the field adopts a second operating condition, the second operating condition corresponding to the combination of the calibration position of the device and the second operating configuration of the collimator;

a second incidence step during which the field, while in the second operating condition, strikes the detection surface, in such a way that the intersection section has a second geometrical configuration relative to the detection surface;

a second acquisition step during which a second image is automatically acquired, the second image being revealed by the detector during the second incidence step;

a second detection step during which the second geometrical configuration is detected automatically by analysis of the second image;

a calculation step during which the local mathematical relationship corresponding to the calibration position is automatically calculated, the local mathematical relationship corresponding to the calibration position correlating mathematically to each other, for the calibration position of the device, the variation of the operating configuration of the collimator and the variation of the geometrical configuration of the intersection section, the calculation step being performed on the basis of the first detecting step and the second detecting step;

wherein:

the first setting-up step is performed by varying the respective positions of the plurality of blades of the collimator, in such a way that the first operating configuration corresponds to a first combination of positions of the respective blades relative to the source;

the second setting-up step is performed by varying the respective positions of the blades, in such a way that the second operating configuration corresponds to a second combination of positions of the respective blades relative to the source;

the first geometrical configuration corresponds to a first combination of positions of respective sectors of the edge of the intersection section relative to the detection surface, the edge delimiting the intersection section;

the second geometrical configuration corresponds to a second combination of positions of the respective sectors of the edge of the intersection section relative to the detection surface;

a step of implementing in the interface a selection function for selecting a desired geometrical configuration of the intersection section relative to the detection surface;

wherein the implementation step takes place by at least:

a step for receiving at least one item of geometrical data representing the desired geometrical configuration;

an obtaining step during which, as a function of the at least one item of geometrical data and by the local mathematical relationship calculated during the calibration method, the operating configuration of the collimator corresponding to the desired geometrical configuration is automatically obtained.

2. The calibration method according to claim 1, comprising:

performing the operating sequence of calibration for each of a group of calibration positions of the device relative to the detection surface;

a further calculating step during which, on the basis of the local mathematical relationships calculated, an intermediate mathematical relationship is automatically calculated which correlates mathematically to each other a variation of the position of the device and the variation of the local mathematical relationship.

3. A method for programming an interface of an apparatus for X-ray analysis, the programming method comprising:

the calibration method according to claim 2, the calibration method being performed for calibrating the collimator of the apparatus;

a step of implementing in the interface a selection function, the selection function being for selecting a desired geometrical configuration of the intersection section relative to the detection surface and a desired position of the device relative to the detection surface;

wherein the implementation step takes place by at least:

a receiving step, during which at least one item of geometrical data representing the desired geometrical configuration and at least one item of position data representing the desired position are received;

a first obtaining step during which, as a function of the at least one item of position data and by the intermediate mathematical relationship calculated during the calibration method, the local mathematical relationship corresponding to the desired position is automatically obtained, the local mathematical relationship corresponding to the desired position correlating mathematically to each other, for the desired position of the device, the variation of the operating configuration of the collimator and the variation of the geometrical configuration of the intersection section;

a second obtaining step during which, as a function of the at least one item of geometrical data and by the local mathematical relationship corresponding to the desired position, the operating configuration of the collimator corresponding to the desired geometrical configuration is automatically obtained.

4. The calibration method according to claim 1, wherein the mathematical relationship includes determining a relationship between a distance from the edge of the detection surface to an edge of the intersection section.

5. The calibration method according to claim 1, wherein, in the calibration position, the device source is oriented at a non-normal angle to the detection surface.

6. The calibration method according to claim 1, wherein:

the first setting-up step is performed by varying the respective operating parameters of the plurality of motors of the collimator, in such a way that the first operating configuration corresponds to a first combination of operating parameters of the respective motors;

the second setting-up step is performed by varying the respective operating parameters of the motors in such a way that the second operating configuration corresponds to a second combination of operating parameters of the respective motors;

the local mathematical relationship comprises at least one local mathematical function which correlates mathematically to each other, for the calibration position of the device, the position relative to the detection surface of one of the sectors and the operating parameter of one of the motors.

7. The calibration method according to claim 6, comprising:
performing the operating sequence of calibration for each of a group of calibration positions of the device relative to the detection surface;
a further calculating step during which, on the basis of the local mathematical relationships calculated, an intermediate mathematical relationship is automatically calculated which correlates mathematically to each other a variation of the position of the device and the variation of the local mathematical relationship.

8. A method for programming an interface of an apparatus for X-ray analysis, the programming method comprising:
the calibration method according to claim 7, the calibration method being performed for calibrating the collimator of the apparatus;
a step of implementing in the interface a selection function, the selection function being for selecting a desired geometrical configuration of the intersection section relative to the detection surface and a desired position of the device relative to the detection surface;
wherein the implementation step takes place by at least:
a receiving step, during which at least one item of geometrical data representing the desired geometrical configuration and at least one item of position data representing the desired position are received;
a first obtaining step during which, as a function of the at least one item of position data and by the intermediate mathematical relationship calculated during the calibration method, the local mathematical relationship corresponding to the desired position is automatically obtained, the local mathematical relationship corresponding to the desired position correlating mathematically to each other, for the desired position of the device, the variation of the operating configuration of the collimator and the variation of the geometrical configuration of the intersection section;
a second obtaining step during which, as a function of the at least one item of geometrical data and by the local mathematical relationship corresponding to the desired position, the operating configuration of the collimator corresponding to the desired geometrical configuration is automatically obtained.

9. The calibration method according to claim 1, comprising:
performing the operating sequence of calibration for each of a group of calibration positions of the device relative to the detection surface;
a further calculating step during which, on the basis of the local mathematical relationships calculated, an intermediate mathematical relationship is automatically calculated which correlates mathematically to each other a variation of the position of the device and the variation of the local mathematical relationship.

10. A method for programming an interface of an apparatus for X-ray analysis, the programming method comprising:
a method for calibrating a collimator for the collimation of X-rays, comprising:
providing a device generating a field of X-rays, the device comprising a source and a collimator and being configured so that the collimator collimates the rays of the source in such a way as to define a field of X-rays;
providing a detector comprising a detection surface and configured to reveal at least one image of the detection surface, the at least one image being representative of the X-rays incident on the detection surface;
providing that the collimator comprises a plurality of blades the collimator being configured so as to cause a variation of the position of each of the blades relative to the source, in such a way that the variation of the operating configuration of the collimator corresponds to a variation of a combination of positions of the respective blades relative to the source;
providing that the intersection section has an edge which delimits the intersection section and which comprises a plurality of sectors of the edge;
providing that each sector of the sectors is associated with a respective one of the blades, in such a way that the variation of the position relative to the source of any of the blades causes a variation of the position relative to the detection surface of the sector associated with the any of the blades, the variation of the geometrical configuration of the intersection section corresponding to a variation of the combination of positions of the respective sectors relative to the detection surface;
providing that the collimator comprises a plurality of motors to cause the variation of the position of each of the blades relative to the source;
providing that each of the motors is associated with a respective one of the blades, so that a variation of an operating parameter of any of the motors causes the variation of the position relative to the source of the blade to which the any motor is associated, the collimator being in this way configured so that a variation of the combination of operating parameters of the respective motors causes the variation of the combination of the respective positions of the blades relative to the source;
providing a local mathematical relationship for each of the blades, comprising a local mathematical function associated with the detection surface, the local mathematical function correlating mathematically to each other, for that calibration position of the device, the position relative to an edge of the detection surface of the sector associated with the blade and the operating parameter of the motor associated with the blade;
for at least one calibration position of the device relative to the detection surface, a calibration operating sequence, the operating sequence being for calibrating the collimator and comprising:
a positioning step during which the device is automatically positioned in the calibration position;
a generating step during which the source automatically generates the X-rays;
a first setting-up step during which the collimator is automatically set in a first operating configuration of the plurality of operating configurations;
a first collimation step during which the collimator, while in the first operating configuration, is such that the field adopts a first operating condition, the first operating condition corresponding to the combination of the calibration position of the device and the first operating configuration of the collimator;
a first incidence step during which the field, while in the first operating condition, strikes the detection surface, in such a way that the intersection section has a first geometrical configuration relative to the detection surface;

a first acquisition step during which a first image is automatically acquired, the first image being revealed by the detector during the first incidence step;

a first detection step during which the first geometrical configuration is detected automatically by analysis of the first image;

a second setting-up step during which the collimator is automatically set in a second operating configuration of the plurality of operating configurations;

a second collimation step during which the collimator, while in the second operating configuration, is such that the field adopts a second operating condition, the second operating condition corresponding to the combination of the calibration position of the device and the second operating configuration of the collimator;

a second incidence step during which the field, while in the second operating condition, strikes the detection surface, in such a way that the intersection section has a second geometrical configuration relative to the detection surface;

a second acquisition step during which a second image is automatically acquired, the second image being revealed by the detector during the second incidence step;

a second detection step during which the second geometrical configuration is detected automatically b analysis of the second image;

a calculation step during which the local mathematical relationship corresponding to the calibration position is automatically calculated, the local mathematical relationship corresponding to the calibration position correlating mathematically to each other, for the calibration position of the device, the variation of the operating configuration of the collimator and the variation of the geometrical configuration of the intersection section, the calculation step being performed on the basis of the first detecting step and the second detecting step;

wherein:

the first setting-up step is performed by varying the respective positions of the plurality of blades of the collimator, in such a way that the first operating configuration corresponds to a first combination of positions of the respective blades relative to the source;

the second setting-up step is performed by varying the respective positions of the blades, in such a way that the second operating configuration corresponds to a second combination of positions of the respective blades relative to the source;

the first geometrical configuration corresponds to a first combination of positions of respective sectors of the edge of the intersection section relative to the detection surface, the edge delimiting the intersection section;

the second geometrical configuration corresponds to a second combination of positions of the respective sectors of the edge of the intersection section relative to the detection surface;

performing the operating sequence of calibration for each of a group of calibration positions of the device relative to the detection surface;

a further calculating step during which on the basis of the local mathematical relationships calculated an intermediate mathematical relationship is automatically calculated which correlates mathematically to each other a variation of the position of the device and the variation of the local mathematical relationship;

a step of implementing in the interface a selection function, the selection function being for selecting a desired geometrical configuration of the intersection section relative to the detection surface and a desired position of the device relative to the detection surface;

wherein the implementation step takes place by at least:

a receiving step, during which at least one item of geometrical data representing the desired geometrical configuration and at least one item of position data representing the desired position are received;

a first obtaining step during which, as a function of the at least one item of position data and by the intermediate mathematical relationship calculated during the calibration method, the local mathematical relationship corresponding to the desired position is automatically obtained, the local mathematical relationship corresponding to the desired position correlating mathematically to each other, for the desired position of the device, the variation of the operating configuration of the collimator and the variation of the geometrical configuration of the intersection section;

a second obtaining step during which, as a function of the at least one item of geometrical data and by the local mathematical relationship corresponding to the desired position, the operating configuration of the collimator corresponding to the desired geometrical configuration is automatically obtained.

* * * * *